(12) United States Patent
Lochmann et al.

(10) Patent No.: US 11,492,321 B2
(45) Date of Patent: Nov. 8, 2022

(54) METHOD FOR PRODUCING CAPPED 3-HYDROXYCARBOXYLIC ACIDS AND THEIR SALTS AND ESTERS

(71) Applicant: IOI Oleo GmbH, Witten (DE)

(72) Inventors: Dirk Lochmann, Witten (DE); Sebastian Reyer, Witten (DE); Michael Stehr, Witten (DE)

(73) Assignee: IOI Oleo GmbH

( * ) Notice: Subject to any disclaimer, the term of this patent is extended or adjusted under 35 U.S.C. 154(b) by 0 days.

(21) Appl. No.: 17/378,950

(22) PCT Filed: Jan. 23, 2019

(86) PCT No.: PCT/EP2019/051543
§ 371 (c)(1),
(2) Date: Jul. 19, 2021

(87) PCT Pub. No.: WO2020/147981
PCT Pub. Date: Jul. 23, 2020

(65) Prior Publication Data
US 2022/0055978 A1  Feb. 24, 2022

(30) Foreign Application Priority Data
Jan. 17, 2019  (WO) ............... PCT/EP2019/051123

(51) Int. Cl.
*C07C 67/10*  (2006.01)

(52) U.S. Cl.
CPC ................... *C07C 67/10* (2013.01)

(58) Field of Classification Search
CPC ..................................... C07C 67/10
See application file for complete search history.

(56) References Cited

U.S. PATENT DOCUMENTS 2,026,985 A  1/1936  Malm

FOREIGN PATENT DOCUMENTS

| DE | 3873016 | 3/1993 |
|---|---|---|
| WO | 2014099300 | 6/2014 |
| WO | 2017213999 | 12/2017 |

OTHER PUBLICATIONS

Zhang, B., et al., Cofactor recycling mechanism in asymmetric biocatalytic reduction of carbonyl compounds mediated by yeast: Which is the efficient electron?, Chemistry—A European Journal, vol. 9, pp. 3604-3610 (Year: 2003).*

* cited by examiner

*Primary Examiner* — Yate' K Cutliff
(74) *Attorney, Agent, or Firm* — Edward E. Sowers; Brannon Sowers & Cracraft PC

(57) ABSTRACT

The invention relates to a method for producing capped (blocked) 3-hydroxybutyric acids and their salts and esters, as well as the products obtainable in this way and their use.

12 Claims, No Drawings

METHOD FOR PRODUCING CAPPED 3-HYDROXYCARBOXYLIC ACIDS AND THEIR SALTS AND ESTERS

CROSS-REFERENCES TO RELATED APPLICATIONS

This application is a National Stage filing of International Application PCT/EP 2019/051543 filed Jan. 23, 2019, entitled "PROCESS FOR PREPARING CAPPED 3-HYDROXYCARBOXYLIC ACIDS AND THEIR SALTS AND ESTERS", claiming priority to PCT/EP 2019/051123, filed Jan. 17, 2019. The subject application claims priority to PCT/EP 2019/051543 and PCT/EP 2019/051123, and incorporates all by reference herein, in their entirety.

BACKGROUND OF THE INVENTION

The present invention relates to the field of keto bodies and related metabolism and the therapy of related diseases.

Especially, the present invention relates to a method for producing capped or blocked 3-hydroxybutyric acids as well as their salts and esters as well as the reaction products thus obtainable or thus prepared (i.e. capped or blocked 3-hydroxybutyric acids as well as their salts and esters) and their use, especially in pharmaceutical compositions, such as drugs or medicaments, or in food and/or food products, as well as their further applications or uses.

Furthermore, the present invention relates to pharmaceutical compositions, especially drugs or medicaments, comprising the reaction products (i.e. capped or blocked 3-hydroxybutyric acids as well as their salts and esters) obtainable or produced according to the inventive method, as well as their applications or uses.

Moreover, the present invention relates to food and/or food products, especially food supplements, functional foods, novel foods, food additives, food supplements, dietary foods, power snacks, appetite suppressants and strength and/or endurance sports supplements, which comprise the reaction products (i.e. capped or blocked 3-hydroxybutyric acids as well as their salts and esters) obtainable or produced according to the inventive method, as well as their applications or uses.

Finally, the present invention relates to a method for producing particular carboxylic acid anhydrides which are suitable as starting materials for the production method according to the invention.

In the human energy metabolism, glucose is the short-term available energy carrier, which is metabolized into energy in the mitochondria by releasing water and carbon dioxide. The glycogen stores of the liver are already emptied during the sleep period during the night. However, especially the human central nervous system (CNS) and the heart require a permanent energy supply.

The physiological alternative to glucose, which is mainly available to the central nervous system, are the so-called keto bodies (synonymously also called ketone bodies).

The term keto body is especially a collective term for three compounds, which are formed mainly in catabolic metabolic states (such as hunger, reduction diets or low-carbohydrate diets) and may lead to ketosis. The term keto bodies includes especially the three compounds acetoacetate (synonymously also referred to as acetacetate) and acetone as well as 3-hydroxybutyric acid (hereinafter also synonymously referred to as beta-hydroxybutyric acid or BHB or 3-BHB) or its salt (i.e. 3-hydroxybutyrate or beta-hydroxybutyrate), the latter being the most important of the three aforementioned compounds. 3-Hydroxybutyric acid or its salt occurs physiologically as the (R)-enantiomer, i.e. as (R)-3-hydroxybutyric acid (synonymously also called (3R)-3-hydroxybutyric acid to emphasize the center of chirality in the 3-position) or its salt.

These keto bodies are also provided physiologically in large amounts from lipids stored in the body by lipolysis during fasting or starvation and replace the energy source glucose almost completely.

The keto bodies are formed in the liver from acetyl coenzyme A (=acetyl-CoA), which originates from beta-oxidation; they represent a transportable form of the acetyl coenzyme A in the human body. However, in order to utilize the keto bodies, the brain and muscles must first adapt by expressing enzymes that are required to convert keto bodies back into acetyl coenzyme A. Especially in times of hunger, the keto bodies contribute a considerable amount to energy production. For example, after some time the brain is able to get by with only a third of the daily amount of glucose.

Physiologically, the keto bodies are synthesized from two molecules of activated acetic acid in the form of acetyl coenzyme A, the normal intermediate product of fatty acid degradation, which is extended using a further acetyl coenzyme A unit and the enzyme HMG-CoA-synthase to the intermediate product 3-hydroxy-3-methyl-glutaryl-CoA (HMG-CoA), wherein finally the HMG-CoA-lyase cleaves off the acetoacetate. These three steps take place exclusively in the mitochondria of the liver (lynen cycle), wherein 3-hydroxybutyrate is finally formed in the cytosol by the D-beta-hydroxybutyrate dehydrogenase. HMG-CoA is also an end product of the degradation of the amino acid leucine, while acetoacetate is formed during the degradation of the amino acids phenylalanine and tyrosine.

Spontaneous decarboxylation turns acetoacetate into acetone; it can occasionally be perceived in the breath of diabetics and dieters. It cannot be further used by the body. However, the proportion of acetone in the keto bodies is small.

Acetoacetate is thus reductively converted into the physiologically relevant form of 3-hydroxybutyric acid or 3-hydroxybutyrate, but can also decompose into the physiologically unusable acetone with the release of carbon dioxide, which is detectable and olfactory perceptible in severe ketosis, a ketoacidosis (e. g. in diabetes mellitus type 1 patients without insulin substitution), in the urine and in the exhaled air.

3-Hydroxybutyric acid is currently used and marketed in the weight training sector as a sodium, magnesium or calcium salt.

However, 3-hydroxybutyric acid is not known or only in very small quantities to humans in evolutionary terms, since plants do not produce 3-hydroxybutyric acid and 3-hydroxybutyric acid in the animal organism only occurs in dead emaciated animals in ketosis, so that 3-hydroxybutyric acid causes nausea when administered orally. 3-Hydroxybutyric acid in the form of free acid and its salts also taste very bitter and can cause severe vomiting and nausea.

Moreover, patients, especially newborns, but also adults cannot permanently tolerate large amounts of salts of 3-hydroxybutyric acid, as these compounds can have a kidney-damaging effect.

In addition, the plasma half-life of 3-hydroxybutyric acid and its salts is so short that even if several grams are taken, the ketosis lasts only for about three to four hours, i.e. patients cannot benefit continuously from a therapy with 3-hydroxybutyric acid or its salts, especially at night. In case of metabolic diseases this can lead to life-threatening situations.

Therefore, in the case of the therapy of such metabolic diseases, so-called medium-chain triglycerides, so-called MCTs, are currently used for ketogenic therapy, i.e. the metabolic conversion of caproic, caprylic and capric acid (i.e. of saturated linear $C_6$-, $C_8$- and $C_{10}$-fatty acids) from the corresponding triglycerides is intended.

Basically, however, from a pharmaceutical and clinical point of view, 3-hydroxybutyric acid is a more effective pharmaceutical-pharmacological target molecule, which, according to the prior art, could in principle be used for the therapy of a large number of diseases, but cannot be used due to its lack of physiological compatibility (e. g. in diseases in connection with a malfunction of the energy metabolism, especially keto-body metabolism, or neurodegenerative diseases such as dementia, Alzheimer's disease, Parkinson's disease, etc., lipometabolic diseases etc.).

The following table illustrates purely exemplary, but by no means limiting, potential therapy options or possible indications for the active ingredient 3-hydroxybutyric acid.

| Indication | Therapeutic effect |
| --- | --- |
| Traumatic brain injury | Under BHB the apoptosis and necrosis rate of nerve cells decreases. |
| Stroke | Under BHB the apoptosis and necrosis rate of nerve cells decreases. |
| Refeeding syndrome | In case of anorexia, discontinuation of enteral or parenteral nutrition and after long periods of hunger, the consumption of starch or glucose can lead to death (see also WHO scheme peanut paste). BHB can be used here as a therapeutic agent to achieve normal food intake more quickly. |
| Appetite suppressant | BHB suppresses the feeling of hunger in the central nervous system (CNS). |
| Epilepsy | Conventional ketogenic diet to significantly reduce the frequency of seizures has extremely poor patient tolerance. BHB offers an immediately effective alternative here. |
| Alzheimer's disease, dementia | Under BHB patients show better cognitive performance. BHB is also effective in the prevention of neurodegenerative diseases. |
| Disorders of fatty acid oxidation (e, g. electron transfer protein defect) | Compensation of a nutrient deficiency in case of defect in energy metabolism. |

Therefore, it is desirable from a pharmaceutical and clinical point of view to be able to find effective precursors or metabolites which physiologically allow direct or indirect access to 3-hydroxybutyric acid or its salts, especially in the physiological metabolism of the human or animal body.

Consequently, the prior art has not lacked attempts to find physiologically suitable precursors or metabolites for 3-hydroxybutyric acid or its salts. So far, however, no efficient compounds have been found in the prior art. Also, access to such compounds is not or not readily possible according to the prior art.

BRIEF SUMMARY OF THE INVENTION

The problem underlying the present invention is thus the provision of an efficient method for producing physiologically suitable or physiologically compatible precursors and/or metabolites of 3-hydroxybutyric acid (i.e. beta-hydroxybutyric acid or BHB or 3-BHB) or their salts.

Such method should especially make the respective BHB precursors and/or BHB metabolites accessible in an efficient way, especially in larger quantities and without significant amounts of toxic by-products.

In a completely surprising way, the applicant has now discovered that capped or blocked 3-hydroxybutyric acids as well as their salts and esters represent an efficient and physiologically effective or physiologically compatible precursor and/or metabolite for the keto body 3-hydroxybutyric acid or its salts and has in this context been able to find or develop an efficient method for producing these compounds, which allows direct and effective, especially economic as well as industrially feasible access to these compounds.

To solve the problem described above, the present invention therefore proposes—according to a first aspect of the present invention—a method for producing capped (blocked) 3-hydroxybutyric acid (beta-hydroxybutyric acid, BHB and/or 3-BHB) or its salts or esters according to claims provided; further, especially special and/or advantageous embodiments of the inventive method are the subject-matter of the relevant claims.

Furthermore, the present invention relates—according to a second aspect of the present invention—to a reaction product obtainable according to the inventive method or a capped (blocked) 3-hydroxybutyric acid (beta-hydroxybutyric acid, BHB and/or 3-BHB) or its salt or ester or a mixture of at least two, especially at least three, capped (blocked) 3-hydroxybutyric acids (beta-hydroxybutyric acids, BHB and/or 3-BHB) or their salts or esters; further, especially special and/or advantageous embodiments of this aspect of the invention are similarly described.

Moreover, the present invention—according to a third aspect of the present invention—relates to a method for producing a carboxylic acid provided; further, especially special and/or advantageous embodiments of this aspect of the invention are also described.

Likewise, the present invention—according to a fourth aspect of the present invention—relates to a pharmaceutical composition, especially a drug or medicament is provided; further, especially special and/or advantageous embodiments of this aspect of the invention are described.

Furthermore, the present invention—according to a fifth aspect of the present invention—relates to an inventive reaction product or an inventive capped (blocked) 3-hydroxybutyric acid (beta-hydroxybutyric acid, BHB and/or 3-BHB) or its salt or ester or an inventive mixture of at least two, especially at least three, different capped (blocked) 3-hydroxybutyric acids (beta-hydroxybutyric acids, BHB and/or 3-BHB) or their salts or esters for the prophylactic and/or therapeutic treatment or for the use in the prophylactic and/or therapeutic treatment of diseases of the human or animal body.

Furthermore, the present invention—according to a sixth aspect of the present invention—relates to the use of an inventive reaction product or an inventive capped (blocked) 3-hydroxybutyric acid (beta-hydroxybutyric acid, BHB and/or 3-BHB) or its salt or ester or an inventive mixture of at least two, especially at least three, different capped (blocked) 3-hydroxybutyric acids (beta-hydroxybutyric acids, BHB and/or 3-BHB) or their salts or esters for the prophylactic and/or therapeutic treatment or for producing a medicament for the prophylactic and/or therapeutic treatment of diseases of the human or animal.

Furthermore, the present invention—according to a seventh aspect of the present invention—relates to the use of an inventive reaction product or an inventive capped (blocked) 3-hydroxybutyric acid (beta-hydroxybutyric acid, BHB and/ or 3-BHB) or its salt or ester or an inventive mixture of at least two, especially at least three, different capped (blocked) 3-hydroxybutyric acids (beta-hydroxybutyric acids, BHB and/or 3-BHB) or their salts or esters.

Furthermore, the present invention—according to an eighth aspect of the present invention—relates to a food and/or food product, especially special and/or advantageous embodiments of the food and/or food product according to the invention.

Finally, the present invention—according to a ninth aspect of the present invention—relates to the use of a an inventive reaction product or an inventive capped (blocked) 3-hydroxybutyric acid (beta-hydroxybutyric acid, BHB and/or 3-BHB) or its salt or ester or an inventive mixture of at least two, especially at least three, different capped (blocked) 3-hydroxybutyric acids (beta-hydroxybutyric acids, BHB and/or 3-BHB) or their salts or esters in a food and/or a food product, especially special and/or advantageous embodiments of the use according to the invention.

It goes without saying that following features, embodiments, advantages and the like, which are subsequently listed below only with regard to one aspect of the invention for the purpose of avoiding repetition, naturally also apply accordingly to the other aspects of the invention, without this requiring a separate mention.

Furthermore, it goes without saying that individual aspects and embodiments of the present invention are also considered disclosed in any combination with other aspects and embodiments of the present invention and, especially, any combination of features and embodiments, as it results from back references of all patent claims, is also considered extensively disclosed with regard to all resulting combination possibilities.

With respect to all relative or percentage weight-based data provided below, especially relative quantity or weight data, it should further be noted that within the scope of the present invention these are to be selected by the person skilled in the art such that they always add up to 100% or 100% by weight, respectively, including all components or ingredients, especially as defined below; however, this is self-evident for the person skilled in the art.

In addition, the skilled person may, if necessary, deviate from the following range specifications without leaving the scope of the present invention.

In addition, it applies that all values or parameters or the like specified in the following can be determined or identified in principle with standardized or explicitly specified determination methods or otherwise with the determination or measurement methods that are otherwise familiar to a person skilled in the art.

Having stated this, the present invention will be described in more detail hereinafter:

DETAILED DESCRIPTION OF THE INVENTION

The subject-matter of the present invention—according to a first aspect of the present invention—is thus a method for producing capped (blocked) 3-hydroxybutyric acid (beta-hydroxybutyric acid, BHB and/or 3-BHB) or its salts or esters, wherein at least one compound of the general formula (I)

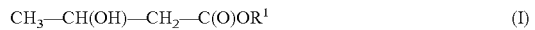

wherein in the general formula (I) the radical $R^1$ represents hydrogen or $C_1$-$C_4$-alkyl, especially $C_1$-$C_4$-alkyl, preferably methyl or ethyl, more preferably ethyl, is reacted with at least one carboxylic acid anhydride of the general formula (II)

wherein in the general formula (II) the radicals $R^2$ and $R^3$, each independently of one another, represent $C_1$-$C_{30}$-alkyl, especially a linear (straight-chain) or branched, saturated or mono- or polyunsaturated $C_1$-$C_{30}$-alkyl, preferentially $C_1$-$C_{21}$-alkyl, preferably a linear (straight-chain) or branched, saturated or mono- or polyunsaturated $C_1$-$C_{21}$-alkyl, more preferably $C_3$-$C_{21}$-alkyl, even more preferably a linear (straight-chain) or branched, saturated or mono- or polyunsaturated $C_3$-$C_{21}$-alkyl, optionally followed by hydrolysis in the case that $R^1$ represents hydrogen, so that, as reaction product, there is/are obtained one or more capped (blocked) 3-hydroxybutyric acids and/or their salts and/or esters of the general formula (III)

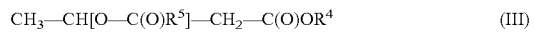

wherein in the general formula (III) the radical $R^4$ represents a radical $R^1$ having the meaning defined hereinabove or a metal ion, especially an alkali metal or alkaline earth metal ion, and the radical $R^5$ represents a radical $R^2$ or $R^3$ each having the meaning defined hereinabove.

As stated above, the applicant has, quite surprisingly, discovered that the capped (=blocked) 3-hydroxybutyric acids or their salts or esters thus produced are efficient, since physiologically compatible precursors and/or metabolites of free 3-hydroxybutyric acid or their salts, which can also be used in larger quantities in pharmaceutical or clinical applications because they are physiologically compatible.

The above-mentioned capped (=blocked) 3-hydroxybutyric acids or their salts or esters, which are accessible for the first time in an efficient manner through the production method according to the invention, represent a physiologically and pharmacologically relevant alternative to free 3-hydroxybutyric acid or its salts.

The production of such compounds by means of conventional organic synthesis is complex and costly, since 3-hydroxybutyric acid has an increased tendency to polymerize and to undergo other undesirable side reactions (e. g. dehydration, decomposition, etc.). Within the scope of the present invention, it was possible for the first time to provide an efficiently working production method with which the capped (blocked) 3-hydroxybutyric acids or their salts or esters can be produced without undesired side reactions, especially in a single step.

The inventive method thus makes it possible for the first time to provide non-toxic capped (blocked) 3-hydroxybutyric acids or their salts or esters from known, commercially available and above all physiologically harmless components or educts (starting compounds). The resulting capped 3-hydroxybutyric acids or their salts or esters can be broken down physiologically, especially in the stomach and/or bowl, and release or generate the target molecule "3-hydroxybutyric acid" or its salts as active ingredient or active component.

In addition, the aforementioned capped (blocked) 3-hydroxybutyric acids or their salts or esters also comprise an acceptable taste to ensure compatibility even when administered orally in larger quantities over a longer period of time (e. g. administration of 50 g daily dose or more).

Finally, studies by the applicant show that the inventive capped (blocked) 3-hydroxybutyric acids or their salts or esters are not only efficient precursors or metabolites of free hydroxybutyric acid or salts thereof themselves, but can also be used as reactants for the synthesis of further precursors or metabolites of free hydroxybutyric acid or salts thereof (e.g. glycerides).

Similarly, the production method according to the invention makes it possible to provide the capped (blocked) 3-hydroxybutyric acids or their salts or esters free from toxic impurities.

In addition, with appropriate starting materials, the method can also be carried out enantioselectively. For example, according to the invention, the production method allows the biologically relevant form, i.e. the (R)-enantiomer, to be enriched, especially by enzyme catalysis, as not to burden the renal system of patients when administered orally (i.e. elimination via the kidneys). In principle, however, it is also possible, and under certain conditions may be useful, to enrich the (S)-enantiomer.

In addition, the production method according to the invention, including optional further processing or purification steps, can be operated economically and can also be implemented on a large scale.

Especially, the inventive production method uses commercially available starting compounds and furthermore allows a relatively simple process management even in case of large-scale implementation.

In contrast to conventional prior art production methods, the production method according to the invention does not use such complex starting materials and uses only a single step. Nevertheless, excellent yields are achieved in accordance with the invention, wherein the formation of by-products is minimized or avoided.

In addition, the inventive method is simple and economical. Especially, the method according to the invention is usually carried out in the absence of solvents and/or without any solvent (i.e. as a reaction in mass or as a reaction in substance or as a so-called bulk reaction); consequently, the reaction products obtained are not contaminated with solvent and no solvent has to be removed and disposed of or recycled in a costly and energy-intensive manner after the method or reaction has been carried out. Furthermore, no toxic by-products are formed.

The following general reaction scheme illustrates the production method according to the invention (wherein the radicals $R^1$, $R^2$, $R^3$, $R^4$ and $R^5$ have the meaning defined hereinabove and in case that the starting compound is the free acid, i.e. $R^1$=H, the intermediate hydrolysis step is not shown):

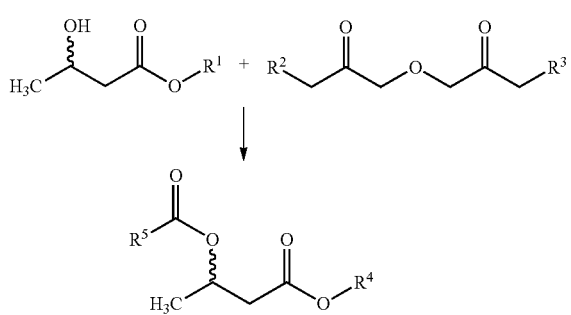

According to a particular embodiment of the present invention, the compound of general formula (I) may be used either in racemic form or else in the form of the (R)-enantiomer. The (R) configuration refers to the chiral carbon atom in the 3-position of the compound of general formula (I).

According to a particular embodiment the compound of general formula (I) is an ester (i.e. in the above formula (I) the radical $R^1$ does not represent hydrogen or the radical $R^1$ represents $C_1$-$C_4$-alkyl).

According to a preferred embodiment of the production method according to the invention, in the above general formula (I) the radical $R^1$ may represent ethyl. In other words, in this preferred embodiment, as a compound of the general formula (I), 3-hydroxybutyric acid ethyl ester (ethyl 3-hydroxybutyrate) of the formula $CH_3$—$CH(OH)$—$CH_2$—$C(O)OC_2H_5$ is used.

For this preferred embodiment, according to which the compound of the general formula (I) is an ethyl ester, the following reaction scheme may be used as an illustration of the reaction course or sequence (wherein in the reaction scheme the radicals $R^2$, $R^3$ and $R^5$ have the meaning defined hereinabove):

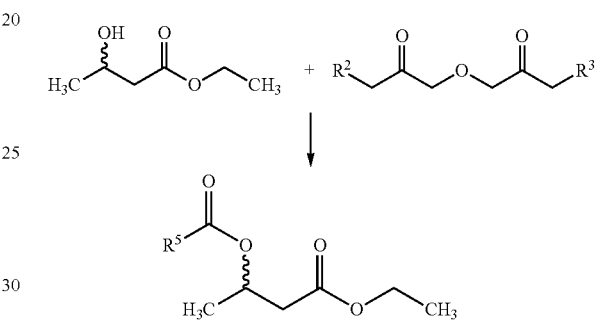

If, according to an alternative particular embodiment, the compound of the general formula (I) is an acid (i.e. in the above general formula (I) the radical $R^1$ represents hydrogen), the following reaction scheme can be used as an illustration of the reaction course or sequence (wherein in the reaction scheme the radicals $R^2$, $R^3$ and $R^5$ have the meaning defined hereinabove), wherein the illustration shows purely by way of example an acidic or neutral hydrolysis leading to the free acid (although in principle a basic hydrolysis leading to the salts of the acid is also possible):

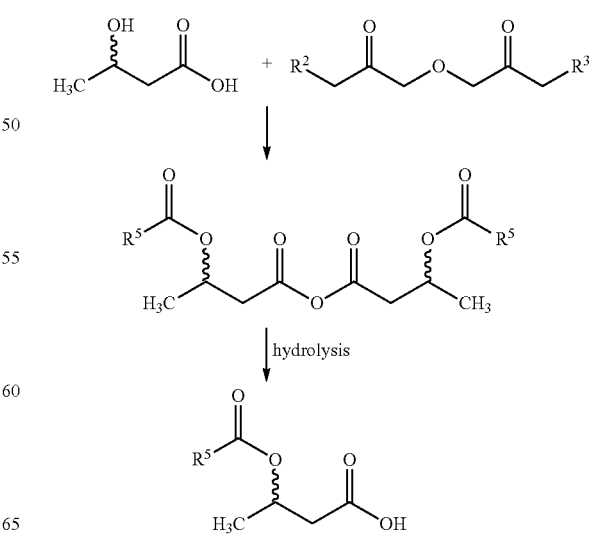

As previously stated, in the case that the compound of general formula (I) is an acid (i.e. in the above general formula (I) the radical $R^1$ represents hydrogen), the hydrolysis can in principle be carried out either under acidic or basic conditions, especially under basic conditions, and/or in the presence of metal ions, especially alkali metal or alkaline earth metal ions.

According to a particular embodiment, as a carboxylic acid anhydride of the general formula (II), a compound in which the radicals $R^2$ and $R^3$ are identical may be used. In other words, as a carboxylic acid anhydride of the general formula (II), a symmetrical carboxylic acid anhydride may be used.

Alternatively, according to another particular embodiment, as a carboxylic acid anhydride of the general formula (II), a compound in which the radicals $R^2$ and $R^3$ are different from one another may be used. In other words, as a carboxylic acid anhydride of the general formula (II), an asymmetric carboxylic acid anhydride may be used.

As far as the reaction temperatures are concerned, these can vary within wide ranges: Especially, the reaction of the at least one compound of the general formula (I) with the at least one carboxylic acid anhydride of the general formula (II) may be carried out at temperatures in the range of from 60 to 150° C., especially in the range of from 70 to 120° C., preferentially in the range of from 80 to 100° C. Nevertheless, it may be necessary, depending on the individual case or the application, to deviate from the above values without leaving the scope of the present invention.

The reaction pressures can also vary within wide ranges: Especially, the reaction of the at least one compound of the general formula (I) with the at least one carboxylic acid anhydride of the general formula (II) may be carried out at a pressure in the range of from 0.0001 bar to 10 bar, especially in the range of from 0.001 bar to 5 bar, preferentially in the range of from 0.01 bar to 2 bar, more preferably in the range of from 0.05 bar to 1 bar, even more preferably at about 1 bar. Nevertheless, it may be necessary, depending on the individual case or the application, to deviate from the above values without leaving the scope of the present invention.

Especially, in the inventive method, the reaction of the at least one compound of the general formula (I) with the at least one carboxylic acid anhydride of the general formula (II) is carried out in the absence of solvents and/or without any solvent. This means that the reaction is carried out as a reaction in mass or as a reaction in substance or as a so-called bulk reaction. This has the advantage that the reaction products obtained are not contaminated with solvent and that no solvent has to be removed and disposed of or recycled in a costly and energy-intensive manner after the method or reaction has been carried out. Surprisingly, the method or reaction nevertheless proceeds with high conversion and yields and at least essentially without significant by-product formation.

In the context of the inventive production method, during the reaction of the at least one compound of the general formula (I) with the at least one carboxylic acid anhydride of the general formula (II), a compound of the general formula (IV)

is formed simultaneously, wherein the radical $R^5$ has the meaning defined hereinabove. Therefore, it may especially be provided according to the invention that the compound of the general formula (IV) is withdrawn during or after the reaction has taken place, especially after the reaction has taken place, preferentially by distillation.

If necessary, the reaction of the at least one compound of the general formula (I) with the at least one carboxylic acid anhydride of the general formula (II) may be followed by purification, especially by means of distillation and/or chromatography, preferentially by means of distillation.

Especially, any starting compounds and reaction by-products still present, especially compounds of the general formula (IV), may be distilled off.

As far as the carboxylic acid anhydride of the general formula (II) used as a starting material is concerned, in principle commercial or commercially available products may be used here (e.g. acetic anhydride) or conventional syntheses may be used for the preparation of the carboxylic acid anhydride of the general formula (II).

However, according to a particular embodiment of the present invention, it is preferred in certain cases according to the invention to proceed as follows for the preparation of the carboxylic acid anhydride of general formula (II):

In the case that in the general formula (II) the radicals $R^2$ and $R^3$ are different from one another, and/or in the case that in the general formula (II) the radicals $R^2$ and $R^3$ each represent an alkyl radical having more than two carbon atoms, the carboxylic acid anhydride of the general formula (II) is obtainable and/or is obtained by reacting acetic anhydride with at least one carboxylic acid of the general formula (IV)

wherein the radical $R^5$ has the meaning defined hereinabove, however, with the proviso that the radicals $R^2$ and $R^3$ are different from one another and/or that the radicals $R^2$ and $R^3$, each independently of one another, represent an alkyl radical having more than two carbon atoms.

In this embodiment, the reaction of acetic anhydride with the at least one carboxylic acid of the general formula (IV) may especially take place according to the reaction equation

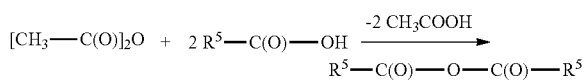

According to a first embodiment of the previously described carboxylic acid anhydride production method, a symmetrical carboxylic acid anhydride of the general formula (II) may be produced. Especially, according to this embodiment, in the general formula (II) the radicals $R^2$ and $R^3$ may be identical and each represent an alkyl radical having more than two carbon atoms.

According to a second, alternative embodiment of the previously described carboxylic acid anhydride production method, an asymmetric carboxylic acid anhydride of the general formula (II) may be produced. Especially, according to this alternative embodiment, in the general formula (II) the radicals $R^2$ and $R^3$ may be different from one another (preferentially wherein in the general formula (II) the radicals $R^2$ and $R^3$ each represent an alkyl radical having more than two carbon atoms).

In the context of the carboxylic acid anhydride production method described hereinabove the reaction of acetic anhydride with the at least one carboxylic acid of the general formula (IV) may be carried out at temperatures in the range of from 60 to 150° C., especially in the range of from 70 to 120° C., preferentially in the range of from 80 to 100° C.

Nevertheless, it may be necessary, depending on the individual case or the application, to deviate from the above values without leaving the scope of the present invention.

Furthermore, in the context of the carboxylic acid anhydride production method described hereinabove, the reaction of acetic anhydride with the at least one carboxylic acid of the general formula (IV) may be carried out at a pressure in the range of from 0.0001 bar to 10 bar, especially in the range of from 0.001 bar to 5 bar, preferentially in the range of from 0.01 bar to 2 bar, more preferably in the range of from 0.05 bar to 1 bar, even more preferably at about 1 bar. Nevertheless, it may be necessary, depending on the individual case or the application, to deviate from the above values without leaving the scope of the present invention.

Within the scope of the production method according to the invention, as a reaction product, one or more capped (blocked) 3-hydroxybutyric acids and/or their salts and/or esters of the general formula (III)

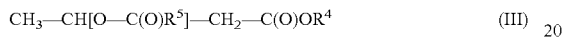

is/are formed,
wherein in the general formula (III)
the radical $R^4$ represents hydrogen or $C_1$-$C_4$-alkyl, especially $C_1$-$C_4$-alkyl, preferably methyl or ethyl, more preferably ethyl, or a metal ion, especially an alkali metal or alkaline earth metal ion,
the radical $R^5$ represents $C_1$-$C_{30}$-alkyl, especially a linear (straight-chain) or branched, saturated or mono- or polyunsaturated $C_1$-$C_{30}$-alkyl, preferentially $C_1$-$C_{21}$-alkyl, preferably a linear (straight-chain) or branched, saturated or mono- or polyunsaturated $C_1$-$C_{21}$-alkyl, more preferably $C_3$-$C_{21}$-alkyl, even more preferably a linear (straight-chain) or branched, saturated or mono- or polyunsaturated $C_3$-$C_{21}$-alkyl.

Especially, in the course of the production method according to the invention, as a reaction product, one or more capped (blocked) 3-hydroxybutyric acid salts and/or esters of the general formula (III)

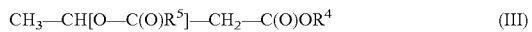

is/are formed,
wherein in the general formula (III)
the radical $R^4$ represents $C_1$-$C_4$-alkyl, especially $C_1$-$C_4$-alkyl, preferably methyl or ethyl, more preferably ethyl, or a metal ion, especially an alkali metal ion or alkaline earth metal ion,
the radical $R^5$ represents $C_1$-$C_{30}$-alkyl, especially a linear (straight-chain) or branched, saturated or mono- or polyunsaturated $C_1$-$C_{30}$-alkyl, preferentially $C_1$-$C_{21}$-alkyl, preferably a linear (straight-chain) or branched, saturated or mono- or polyunsaturated $C_1$-$C_{21}$-alkyl, more preferably $C_3$-$C_{21}$-alkyl, even more preferably a linear (straight-chain) or branched, saturated or mono- or polyunsaturated $C_3$-$C_{21}$-alkyl.

According to a particular embodiment, in the course of the inventive production method, as a reaction product, one or more capped (blocked) 3-hydroxybutyric acid esters of the general formula (III)

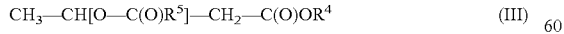

is/are formed,
wherein in the general formula (III)
the radical $R^4$ represents $C_1$-$C_4$-alkyl, especially $C_1$-$C_4$-alkyl, preferably methyl or ethyl, more preferably ethyl,
the radical $R^5$ represents $C_1$-$C_{30}$-alkyl, especially a linear (straight-chain) or branched, saturated or mono- or polyunsaturated $C_1$-$C_{30}$-alkyl, preferentially $C_1$-$C_{21}$-alkyl, preferably a linear (straight-chain) or branched, saturated or mono- or polyunsaturated $C_1$-$C_{21}$-alkyl, more preferably $C_3$-$C_{21}$-alkyl, even more preferably a linear (straight-chain) or branched, saturated or mono- or polyunsaturated $C_3$-$C_{21}$-alkyl.

According to a further particular embodiment, in the course of the inventive production method, as a reaction product, one or more capped (blocked) 3-hydroxybutyric acid esters of the general formula (III)

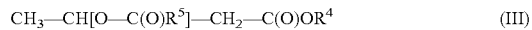

is/are formed,
wherein in the general formula (III)
the radical $R^4$ represents ethyl,
the radical $R^5$ represents $C_1$-$C_{30}$-alkyl, especially a linear (straight-chain) or branched, saturated or mono- or polyunsaturated $C_1$-$C_{30}$-alkyl, preferentially $C_1$-$C_{21}$-alkyl, preferably a linear (straight-chain) or branched, saturated or mono- or polyunsaturated $C_1$-$C_{21}$-alkyl, more preferably $C_3$-$C_{21}$-alkyl, even more preferably a linear (straight-chain) or branched, saturated or mono- or polyunsaturated $C_3$-$C_{21}$-alkyl.

As mentioned hereinbefore, the method according to the invention is usually carried out in the absence of solvents and/or without any solvent (i.e. as a reaction in mass or as a reaction in substance or as a so-called bulk reaction). This has the advantage that the reaction products obtained are not contaminated with solvent and no solvent has to be removed and disposed of or recycled in a costly and energy-intensive manner after the method or reaction has been carried out. Surprisingly, the method or reaction nevertheless proceeds with high conversions and yields and at least essentially without significant by-product formation.

A further subject-matter—according to a second aspect of the present invention—is the reaction product obtainable according to the inventive method or the inventive reaction product (i. e. one or more capped or blocked 3-hydroxybutyric acids and/or their salts and/or esters or mixtures thereof).

Especially, the inventive reaction product may comprise one or more capped (blocked) 3-hydroxybutyric acids and/or their salts and/or esters of the general formula (III)

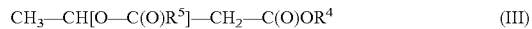

wherein in the general formula (III)
the radical $R^4$ represents hydrogen or $C_1$-$C_4$-alkyl, especially $C_1$-$C_4$-alkyl, preferably methyl or ethyl, more preferably ethyl, or a metal ion, especially an alkali metal ion or alkaline earth metal ion,
the radical $R^5$ represents $C_1$-$C_{30}$-alkyl, especially a linear (straight-chain) or branched, saturated or mono- or polyunsaturated $C_1$-$C_{30}$-alkyl, preferentially $C_1$-$C_{21}$-alkyl, preferably a linear (straight-chain) or branched, saturated or mono- or polyunsaturated $C_1$-$C_{21}$-alkyl, more preferably $C_3$-$C_{21}$-alkyl, even more preferably a linear (straight-chain) or branched, saturated or mono- or polyunsaturated $C_3$-$C_{21}$-alkyl.

According to a particular embodiment, the inventive reaction product may comprise one or more capped (blocked) 3-hydroxybutyric acid salts and/or esters of the general formula (III)

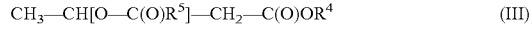

wherein in the general formula (III)
the radical $R^4$ represents $C_1$-$C_4$-alkyl, especially $C_1$-$C_4$-alkyl, preferably methyl or ethyl, more preferably ethyl, or a metal ion, especially an alkali metal ion or alkaline earth metal ion,
the radical $R^5$ represents $C_1$-$C_{30}$-alkyl, especially a linear (straight-chain) or branched, saturated or mono- or polyunsaturated $C_1$-$C_{30}$-alkyl, preferentially $C_1$-$C_{21}$-alkyl, preferably a linear (straight-chain) or branched, saturated or mono- or polyunsaturated $C_1$-$C_{21}$-alkyl, more preferably $C_3$-$C_{21}$-alkyl, even more preferably a linear (straight-chain) or branched, saturated or mono- or polyunsaturated $C_3$-$C_{21}$-alkyl.

According to a further particular embodiment, the reaction product according to the invention may comprise one or more capped (blocked) 3-hydroxybutyric acid esters of the general formula (III)

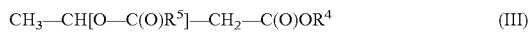

wherein in the general formula (III)
the radical $R^4$ represents $C_1$-$C_4$-alkyl, especially $C_1$-$C_4$-alkyl, preferably methyl or ethyl, more preferably ethyl,
the radical $R^5$ represents $C_1$-$C_{30}$-alkyl, especially a linear (straight-chain) or branched, saturated or mono- or polyunsaturated $C_1$-$C_{30}$-alkyl, preferentially $C_1$-$C_{21}$-alkyl, preferably a linear (straight-chain) or branched, saturated or mono- or polyunsaturated $C_1$-$C_{21}$-alkyl, more preferably $C_3$-$C_{21}$-alkyl, even more preferably a linear (straight-chain) or branched, saturated or mono- or polyunsaturated $C_3$-$C_{21}$-alkyl.

According to yet another particular embodiment, the reaction product according to the invention may comprise one or more capped (blocked) 3-hydroxybutyric acid esters of the general formula (III)

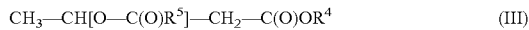

wherein in the general formula (III)
the radical $R^4$ represents ethyl,
the radical $R^5$ represents $C_1$-$C_{30}$-alkyl, especially a linear (straight-chain) or branched, saturated or mono- or polyunsaturated $C_1$-$C_{30}$-alkyl, preferentially $C_1$-$C_{21}$-alkyl, preferably a linear (straight-chain) or branched, saturated or mono- or polyunsaturated $C_1$-$C_{21}$-alkyl, more preferably $C_3$-$C_{21}$-alkyl, even more preferably a linear (straight-chain) or branched, saturated or mono- or polyunsaturated $C_3$-$C_{21}$-alkyl.

Furthermore, the inventive reaction product of the general formula (III) may comprise at least two different compounds of the general formula (III).

Especially, the inventive reaction product of the general formula (III) may comprise at least three different compounds of the general formula (III).

A further subject-matter of the present invention according to this aspect of the invention is a capped (blocked) 3-hydroxybutyric acid and/or its salts and/or ester,
wherein the capped (blocked) 3-hydroxybutyric acid and/or its salt and/or ester corresponds to the general formula (III)

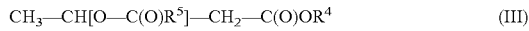

wherein in the general formula (III)
the radical $R^4$ represents hydrogen or $C_1$-$C_4$-alkyl, especially $C_1$-$C_4$-alkyl, preferably methyl or ethyl, more preferably ethyl, or a metal ion, especially an alkali metal ion or alkaline earth metal ion, the radical $R^5$ represents $C_1$-$C_{30}$-alkyl, especially a linear (straight-chain) or branched, saturated or mono- or polyunsaturated $C_1$-$C_{30}$-alkyl, preferentially $C_1$-$C_{21}$-alkyl, preferably a linear (straight-chain) or branched, saturated or mono- or polyunsaturated $C_1$-$C_{21}$-alkyl, more preferably $C_3$-$C_{21}$-alkyl, even more preferably a linear (straight-chain) or branched, saturated or mono- or polyunsaturated $C_3$-$C_{21}$-alkyl.

Especially, a subject-matter of the present invention according to this aspect of the invention is a salt and/or ester of a capped (blocked) 3-hydroxybutyric acid, especially as defined hereinabove,
wherein the salt and/or ester of the capped (blocked) 3-hydroxybutyric acid corresponds to the general formula (III)

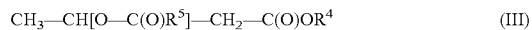

wherein in the general formula (III)
the radical $R^4$ represents $C_1$-$C_4$-alkyl, especially $C_1$-$C_4$-alkyl, preferably methyl or ethyl, more preferably ethyl, or a metal ion, especially an alkali metal ion or alkaline earth metal ion,
the radical $R^5$ represents $C_1$-$C_{30}$-alkyl, especially a linear (straight-chain) or branched, saturated or mono- or polyunsaturated $C_1$-$C_{30}$-alkyl, preferentially $C_1$-$C_{21}$-alkyl, preferably a linear (straight-chain) or branched, saturated or mono- or polyunsaturated $C_1$-$C_{21}$-alkyl, more preferably $C_3$-$C_{21}$-alkyl, even more preferably a linear (straight-chain) or branched, saturated or mono- or polyunsaturated $C_3$-$C_{21}$-alkyl.

According to a particular embodiment, the subject-matter of the present invention according to this aspect of the invention is an ester of a capped (blocked) 3-hydroxybutyric acid, especially as defined hereinabove,
wherein the ester of the capped (blocked) 3-hydroxybutyric acid corresponds to the general formula (III)

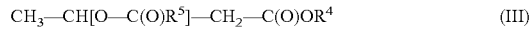

wherein in the general formula (III)
the radical $R^4$ represents $C_1$-$C_4$-alkyl, especially $C_1$-$C_4$-alkyl, preferably methyl or ethyl, more preferably ethyl,
the radical $R^5$ represents $C_1$-$C_{30}$-alkyl, especially a linear (straight-chain) or branched, saturated or mono- or polyunsaturated $C_1$-$C_{30}$-alkyl, preferentially $C_1$-$C_{21}$-alkyl, preferably a linear (straight-chain) or branched, saturated or mono- or polyunsaturated $C_1$-$C_{21}$-alkyl, more preferably $C_3$-$C_{21}$-alkyl, even more preferably a linear (straight-chain) or branched, saturated or mono- or polyunsaturated $C_3$-$C_{21}$-alkyl.

Finally, according to another particular embodiment, the subject-matter of the present invention is an ester of a capped (blocked) 3-hydroxybutyric acid, especially as defined hereinabove,
wherein the ester of the capped (blocked) 3-hydroxybutyric acid corresponds to the general formula (III)

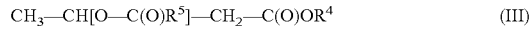

wherein in the general formula (III)
the radical $R^4$ represents ethyl,
the radical $R^5$ represents $C_1$-$C_{30}$-alkyl, especially a linear (straight-chain) or branched, saturated or mono- or polyunsaturated $C_1$-$C_{30}$-alkyl, preferentially $C_1$-$C_{21}$-alkyl, preferably a linear (straight-chain) or branched, saturated or mono- or polyunsaturated $C_1$-$C_{21}$-alkyl, more preferably $C_3$-$C_{21}$-alkyl, even more preferably a linear (straight-chain) or branched, saturated or mono- or polyunsaturated $C_3$-$C_{21}$-alkyl.

A further subject-matter of the present invention according to this aspect of the invention is a mixture comprising at least two different capped (blocked) 3-hydroxybutyric acids and/or their salts and/or esters, as defined hereinabove.

Especially, again, a further subject-matter of the present invention according to this aspect of the invention is a mixture comprising at least three different capped (blocked) 3-hydroxybutyric acids and/or their salts and/or esters, as defined hereinabove.

The reaction product obtainable according to the inventive method or the inventive reaction product as defined hereinabove, respectively, and/or the capped or blocked 3-hydroxybutyric acids and/or their salts and/or esters obtainable according to the inventive method or the inventive capped or blocked 3-hydroxybutyric acids and/or their salts and/or esters as defined hereinabove, respectively, and/or the mixture obtainable according to the inventive production method or the inventive mixture as defined hereinabove, respectively, comprises a multitude of advantages and special features compared to the prior art:

As the applicant has surprisingly found out, the reaction product obtainable according to the inventive method or the inventive reaction product as defined hereinabove, respectively, and/or the capped or blocked 3-hydroxybutyric acids and/or their salts and/or esters obtainable according to the inventive production method or the inventive capped or blocked 3-hydroxybutyric acids and/or their salts and/or esters as defined hereinabove, respectively, and/or the mixture obtainable according to the inventive production method or the inventive mixture as defined hereinabove, respectively, is especially suitable as a precursor or metabolite of 3-hydroxybutyric acid or its salts, since, on the one hand, it is converted physiologically, especially in the gastrointestinal tract, to 3-hydroxybutyric acid or its salts and, on the other hand, it simultaneously comprises a good physiological compatibility or tolerability, especially with regard to non-toxicity and acceptable organoleptic properties.

Moreover, the reaction product obtainable according to the inventive method or the inventive reaction product as defined hereinabove, respectively, and/or the capped or blocked 3-hydroxybutyric acids and/or their salts and/or esters obtainable according to the inventive production method or the inventive capped or blocked 3-hydroxybutyric acids and/or their salts and/or esters as defined hereinabove, respectively, and/or the mixture obtainable according to the inventive production method or the inventive mixture as defined hereinabove, respectively, is easily accessible or available on a large scale on a synthetic basis, even on a commercial scale, and with the required pharmaceutical or pharmacological quality.

Additionally, the reaction product obtainable according to the inventive method or the inventive reaction product as defined hereinabove, respectively, and/or the capped or blocked 3-hydroxybutyric acids and/or their salts and/or esters obtainable according to the inventive production method or the inventive capped or blocked 3-hydroxybutyric acids and/or their salts and/or esters as defined hereinabove, respectively, and/or the mixture obtainable according to the inventive production method or the inventive mixture as defined hereinabove, respectively, can, if necessary, be provided in enantiomerically pure or enantiomerically enriched form.

The reaction product obtainable according to the inventive method or the inventive reaction product as defined hereinabove, respectively, and/or the capped or blocked 3-hydroxybutyric acids and/or their salts and/or esters obtainable according to the inventive production method or the capped or blocked 3-hydroxybutyric acids and/or their salts and/or esters as defined hereinabove, respectively, and/or the mixture obtainable according to the inventive production method or the inventive mixture as defined hereinabove, respectively, thus represents an efficient pharmacological drug target in the context of keto-body therapy of the human or animal body.

In the following, the remaining aspects of the invention are explained in more detail.

A further subject-matter of the present invention—according to a third aspect of the present invention—is a method for producing particular carboxylic acid anhydrides which are suitable as starting compounds for the inventive production method according to the first aspect of the invention.

A subject-matter of the present invention according to this aspect of the invention is a method for producing a carboxylic acid anhydride of the general formula (II)

$$R^2\text{—C(O)—O—C(O)—}R^3 \qquad (II)$$

wherein in the general formula (II) the radicals $R^2$ and $R^3$, each independently of one another, represent $C_1$-$C_{30}$-alkyl, especially a linear (straight-chain) or branched, saturated or mono- or polyunsaturated $C_1$-$C_{30}$-alkyl, preferentially $C_1$-$C_{21}$-alkyl, preferably a linear (straight-chain) or branched, saturated or mono- or polyunsaturated $C_1$-$C_{21}$-alkyl, more preferably $C_3$-$C_{21}$-alkyl, even more preferably a linear (straight-chain) or branched, saturated or mono- or polyunsaturated $C_3$-$C_{21}$-alkyl, however, with the proviso that in the general formula (II) the radicals $R^2$ and $R^3$ are different from one another and/or that in the general formula (II) the radicals $R^2$ and $R^3$ each represent an alkyl radical having more than two carbon atoms, by reacting acetic anhydride with at least one carboxylic acid of the general formula (IV)

$$R^5\text{—C(O)—OH} \qquad (IV)$$

wherein the radical $R^5$ represents a radical $R^2$ or $R^3$ each having the meaning defined hereinabove, however, with the proviso that the radicals $R^2$ and $R^3$ are different from one another and/or that the radicals $R^2$ and $R^3$ each represent an alkyl radical having more than two carbon atoms.

In the inventive carboxylic acid anhydride production method, the reaction of acetic anhydride with the at least one carboxylic acid of the general formula (IV) may especially take place according to the reaction equation $$[CH_3\text{—C(O)}]_2O + 2R^5\text{—C(O)—OH} \xrightarrow{-2\,CH_3COOH} R^5\text{—C(O)—O—C(O)—}R^5$$

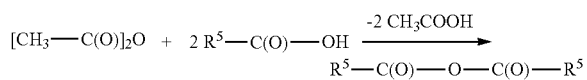

(wherein the radical used in the reaction equation has the meaning defined hereinabove).

According to a particular embodiment of the inventive carboxylic acid anhydride production method, a symmetrical carboxylic acid anhydride of the general formula (II) is produced. In this embodiment, in the above general formula (II) the radicals $R^2$ and $R^3$ are identical and each represent an alkyl radical having more than two carbon atoms.

According to a further particular but alternative embodiment of the inventive carboxylic acid anhydride production method, an asymmetric carboxylic acid anhydride of the general formula (II) is produced. In this embodiment, in the above general formula (II) the radicals $R^2$ and $R^3$ are different from one another, preferentially wherein in the general formula (II) the radicals $R^2$ and $R^3$ each represent an alkyl radical having more than two carbon atoms.

The inventive carboxylic acid anhydride production method is illustrated by the following reaction scheme as an example for the reaction of a $C_3$-$C_{31}$-alkyl monocarboxylic acid with acetic anhydride (wherein the acetic acid formed at the same time is not shown for simplicity):

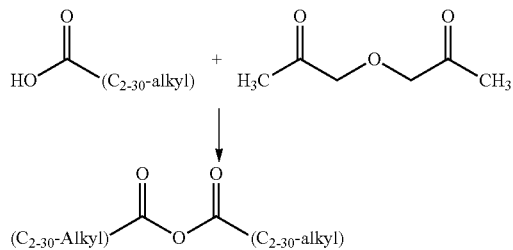

In the context of the carboxylic acid anhydride production method described hereinabove, the reaction of acetic anhydride with the at least one carboxylic acid of the general formula (IV) may be carried out at temperatures in the range of from 60 to 150° C., especially in the range of from 70 to 120° C., preferentially in the range of from 80 to 100° C. Nevertheless, it may be necessary, depending on the individual case or the application, to deviate from the above values without leaving the scope of the present invention.

Furthermore, within the context of the carboxylic acid anhydride production method described above, the reaction of acetic anhydride with the at least one carboxylic acid of the general formula (IV) may be carried out at a pressure in the range of from 0.0001 bar to 10 bar, especially in the range of from 0.001 bar to 5 bar, preferentially in the range of from 0.01 bar to 2 bar, more preferably in the range of from 0.05 bar to 1 bar, even more preferably at about 1 bar. Nevertheless, it may be necessary, depending on the individual case or the application, to deviate from the above values without leaving the scope of the present invention.

Especially, in the carboxylic acid anhydride production method described above, the reaction (i.e. reaction of acetic anhydride with the at least one carboxylic acid of the general formula (IV)) is carried out in the absence of solvents and/or without any solvent I.e. the reaction is thus carried out as a reaction in mass or as a reaction in substance or as a so-called bulk reaction. This has the advantage that the reaction products obtained are not contaminated with solvent and no solvent has to be removed and disposed of or recycled in a costly and energy-intensive manner after the carboxylic acid anhydride production method or reaction has been carried out. Surprisingly, the method or reaction nevertheless proceeds with high conversions and yields and at least essentially without significant by-product formation.

The inventive carboxylic acid anhydride production method proceeds extremely efficient, in particular in a single step, and in particular without the formation of interfering or toxic by-products.

In contrast to this, conventional prior art carboxylic acid anhydride syntheses proceed in a multi-step process and typically proceed via the respective carboxylic acid chlorides, which must first be prepared from the relevant carboxylic acids in an additional process step by means of sulfuryl chloride, wherein the chemicals or by-products and intermediates used in this process are sometimes toxic; moreover, it is a multi-step synthesis which cannot be readily implemented on an industrial scale, especially for safety reasons.

Here, the inventive carboxylic acid anhydride production method offers an efficient and simple alternative that can also be implemented on a large scale.

Therefore, the inventive carboxylic acid anhydride production method provides, for the first time, this new as well as efficient synthesis route for the particular carboxylic acid anhydrides defined hereinbefore.

Again, another subject-matter of the present invention—according to a fourth aspect of the present invention—is a pharmaceutical composition, especially a drug or medicament, which comprises a reaction product obtainable according to the inventive production method or the inventive reaction product as defined hereinabove, respectively, and/or a capped (blocked) 3-hydroxybutyric acid or its salt or ester obtainable according to the inventive production method or the inventive capped (blocked) 3-hydroxybutyric acid or its salt or ester as defined hereinabove, respectively, and/or a mixture obtainable according to the inventive production method or the inventive mixture as defined hereinabove, respectively.

Especially, according to this aspect of the invention, the present invention relates to a pharmaceutical composition for the prophylactic and/or therapeutic treatment or for use in the prophylactic and/or therapeutic treatment of diseases of the human or animal body. This may especially concern diseases associated with a disorder of the energy metabolism, especially keto-body metabolism, such as especially craniocerebral trauma, stroke, hypoxia, cardiovascular diseases such as myocardial infarction, refeeding syndrome, anorexia, epilepsy, neurodegenerative diseases such as dementia, Alzheimer's disease, Parkinson's disease, multiple sclerosis and amyotrophic lateral sclerosis, fat metabolic diseases such as glucose transporter defect (GLUT1 defect), VL-FAOD and mitochondriopathies such as mitochondrial thiolase defect, Huntington's disease, cancers such as T-cell lymphomas, astrocytomas and glioblastomas, HIV, rheumatic diseases such as rheumatoid arthritis and arthritis urica, diseases of the gastrointestinal tract such as chronic inflammatory bowel diseases, especially ulcerative colitis and Crohn's disease, lyosomal storage diseases such as sphingolipidosis, especially Niemann-Pick disease, diabetes mellitus and effects or side-effects of chemotherapy.

Again, a further subject-matter of the present invention—according to a fifth aspect of the present invention—is a reaction product obtainable according to the inventive production method or the inventive reaction product as defined hereinabove, respectively, and/or a capped (blocked) 3-hydroxybutyric acid or its salt or ester obtainable according to the inventive production method or the inventive capped (blocked) 3-hydroxybutyric acid or its salt or ester as defined hereinabove, respectively, and/or a mixture obtainable according to the inventive production method or the inventive mixture as defined hereinabove, respectively, for the prophylactic and/or therapeutic treatment or for use in the prophylactic and/or therapeutic treatment of diseases of the human or animal body, especially diseases associated with a disorder of the energy metabolism, especially keto-body metabolism, such as especially craniocerebral trauma, stroke, hypoxia, cardiovascular diseases such as myocardial infarction, refeeding syndrome, anorexia, epilepsy, neurodegenerative diseases such as dementia, Alzheimer's disease, Parkinson's disease, multiple sclerosis and amyotrophic lateral sclerosis, fat metabolic diseases such as glucose transporter defect (GLUT1 defect), VL-FAOD and mitochondriopathies such as mitochondrial thiolase defect, Huntington's disease, cancers such as T-cell lymphomas, astrocytomas and glioblastomas, HIV, rheumatic diseases such as rheumatoid arthritis and arthritis urica, diseases of the gastrointestinal tract such as chronic inflammatory bowel diseases, especially ulcerative colitis and Crohn's disease, lyosomal storage diseases such as sphingolipidosis, especially Niemann-Pick disease, diabetes mellitus and effects or side-effects of chemotherapy.

Likewise, a further subject-matter of the present invention—according to a sixth aspect of the present invention—is the use of a reaction product obtainable according to the inventive production method or the inventive reaction product as defined hereinabove, respectively, and/or a capped (blocked) 3-hydroxybutyric acid or its salt or ester obtainable according to the inventive production method or the inventive capped (blocked) 3-hydroxybutyric acid its salt or ester as defined hereinabove, respectively, and/or a mixture obtainable according to the inventive production method or the inventive mixture as defined hereinabove, respectively, for the prophylactic and/or therapeutic treatment or for producing a pharmaceutical for the prophylactic and/or therapeutic treatment of diseases of the human or animal body, especially diseases associated with a disorder of the energy metabolism, especially keto-body metabolism, such as especially craniocerebral trauma, stroke, hypoxia, cardiovascular diseases such as myocardial infarction, refeeding syndrome, anorexia, epilepsy, neurodegenerative diseases such as dementia, Alzheimer's disease, Parkinson's disease, multiple sclerosis and amyotrophic lateral sclerosis, fat metabolic diseases such as glucose transporter defect (GLUT1 defect), VL-FAOD and mitochondriopathies such as mitochondrial thiolase defect, Huntington's disease, cancers such as T-cell lymphomas, astrocytomas and glioblastomas, HIV, rheumatic diseases such as rheumatoid arthritis and arthritis urica, diseases of the gastrointestinal tract such as chronic inflammatory bowel diseases, especially ulcerative colitis and Crohn's disease, lyosomal storage diseases such as sphingolipidosis, especially Niemann-Pick disease, diabetes mellitus and effects or side-effects of chemotherapy.

Likewise, a further subject-matter of the present invention—according to a seventh aspect of the present invention—is the use of a reaction product obtainable according to the inventive production method or the inventive reaction product as defined hereinabove, respectively, and/or a capped (blocked) 3-hydroxybutyric acid or its salt or ester obtainable according to the inventive production method or the inventive capped (blocked) 3-hydroxybutyric acid or its salt or ester as defined hereinabove, respectively, and/or a mixture, obtainable according to the inventive production method or the inventive mixture as defined hereinabove, respectively, for the prophylactic and/or therapeutic treatment or for producing a medicament for the prophylactic and/or therapeutic treatment of or for the application for catabolic metabolic states, such as hunger, diets or low-carbohydrate nutrition.

Likewise, a further subject-matter of the present invention—according to an eighth aspect of the present invention—is a food and/or a food product, which comprises a reaction product obtainable according to the inventive production method or the inventive reaction product as defined hereinabove, respectively, and/or a capped (blocked) 3-hydroxybutyric acid or its salt or ester obtainable according to the inventive production method or the inventive capped (blocked) 3-hydroxybutyric acid or its salt or ester as defined hereinabove, respectively, and/or a mixture obtainable according to the inventive production method or the inventive mixture as defined hereinabove, respectively.

According to a particular embodiment, the food and/or the food product may essentially be a dietary supplement, a functional food, a novel food, a food additive, a food supplement, a dietary food, a power snack, an appetite suppressant or a strength and/or endurance sport supplement.

Finally, yet another subject-matter of the present invention—according to a ninth aspect of the present invention—is the use of a reaction product obtainable according to the inventive production method or the inventive reaction product as defined hereinabove, respectively, and/or a capped (blocked) 3-hydroxybutyric acid or its salt or ester obtainable according to the inventive production method or the inventive capped (blocked) 3-hydroxybutyric acid or its salt or ester as defined hereinabove, respectively, and/or a mixture obtainable according to the inventive production method or the inventive mixture as defined hereinabove, respectively, in a food and/or a food product.

According to this aspect of the invention, the food and/or the food product may especially be a dietary supplement, a functional food, a novel food, a food additive, a food supplement, a dietary food, a power snack, an appetite suppressant or a strength and/or endurance sports supplement.

Further embodiments, modifications and variations of the present invention are readily recognizable or realizable by a person skilled in the art when reading the description, without leaving the scope of the present invention.

The present invention is illustrated by the following examples, which are not intended to limit the present invention in any way, but only to explain the exemplary and non-limiting implementation and configuration of the present invention.

EXAMPLES

Examples of Production

The inventive production method is illustrated by the following examples. The relevant general reaction schemes are shown and explained in the general description section.

Production of 3-acetoxybutyric Acid Ethyl Ester (3-Ac-BHB Ethyl Ester) and Application Tests In a 250-ml-multi-neck flask with dephlegmator (partial condenser) and distillation bridge, 50 g of (R)/(S)-3-hydroxybutyric acid ethyl ester (racemic 3-BHB ethyl ester) and 55 g acetic anhydride are provided. The reaction mixture is reacted at 100° C. with stirring and under reflux for 10 h. Then the acetic acid formed and excess acetic anhydride are distilled off under vacuum. A 3-acetoxybutyric acid ethyl ester with 98% purity is obtained.

Characterization is performed by gas chromatography (GC) and GC-MS analysis (gas chromatography with mass spectrometry coupling).

The results of the conversion/time course are summarized in the table below:

| time/h | acetic anhydride/% | 3-BHB ethyl ester/%. | 3-Ac-BHB ethyl ester (product)/%. | unknown/% | Comment |
| --- | --- | --- | --- | --- | --- |
| 1 | 28.8 | 38.9 | 31.3 | 1 | 80° C. |
| 3 | 23.1 | 26.1 | 49.5 | 1.3 | — |
| 6 | 18.6 | 15.9 | 63.9 | 1.6 | temperature increase to 100° C. |

-continued

| time/h | acetic anhydride/% | 3-BHB ethyl ester/%. | 3-Ac-BHB ethyl ester (product)/%. | unknown/% | Comment |
|---|---|---|---|---|---|
| 9 | 12.4 | 3,2 | 82.6 | 1.8 | — |
| 12 | 11.5 | 1.3 | 85.6 | 1.6 | — |
| — | 0 | 0.6 | 97.7 | 1.7 | after distillation |

The taste of 3-acetoxybutyric acid ethyl ester is significantly less unpleasant and bitter than that of pure 3-BHB ethyl ester or even of 3-BHB triglyceride.

Cleavage experiments (splitting experiments) with 3-acetoxybutyric acid ethyl ester in a gastric or intestinal medium (FaSSGF medium simulating the stomach or FaSSIF medium simulating the intestinal tract), each in the presence or absence of pancreatin, demonstrate cleavage to 3-BHB in free form. These cleavage experiments demonstrate that capped (blocked) 3-hydroxybutyric acid or its salts or esters, specifically 3-acetoxybutyric acid ethyl ester in this case, are efficient precursors or metabolites of free hydroxybutyric acid or its salts, especially with respect to their intended effect, which are moreover present in physiologically tolerable or physiologically compatible form.

Further Conversion of 3-acetoxybutyric Acid Ethyl Ester (3-Ac-BHB Ethyl Ester) and Application Tests Furthermore, it can be shown that the 3-acetoxybutyric acid ethyl ester obtained in this way can be used as a starting material with enzyme as catalyst (e.g. immobilized enzyme, such as CALB lipase on polymer support, derived from *Candida antarctica*, e.g. Novozym® 435 from Sigma-Aldrich or Merck or Lipozym® 435 from Strem Chemicals, Inc.) in a transesterification reaction to glycerides (reaction at 50 to 70° C., 24 h 1 wt.-% enzyme). Triacetin is used as a further starting material; since this already contains acetyl groups, no undesirable by-products are formed during any transesterification at the already acetylated OH-group of the 3-BHB ethyl ester. The only by-product formed is ethyl acetate, which can be readily removed. A mixture of mono-, di- and triglycerides of 3-acetoxybutyric acid is formed.

Cleavage experiments (splitting experiments) of this mixture in a gastric or intestinal medium (FaSSGF medium simulating the stomach or FaSSIF medium simulating the intestinal tract), each in the presence or absence of pancreatin, demonstrate cleavage to 3-BHB in free form (cleavage cascade from triglyceride to diglyceride to monoglyceride to free 3-BHB). These cleavage experiments prove that also the glycerides of the capped (blocked) 3-hydroxybutyric acid or its salts are efficient precursors or metabolites of the free 3-hydroxybutyric acid or its salts, especially with regard to their intended effect, which moreover are present in physiologically tolerable or physiologically compatible form.

This shows that capped (blocked) 3-hydroxybutyric acid or its salts or esters are not only efficient precursors or metabolites of free 3-hydroxybutyric acid or its salts themselves, but can also be used as reactants for the synthesis of further precursors or metabolites of free 3-hydroxybutyric acid or its salts.

Further Production Examples and Application Tests

According to the inventive carboxylic acid anhydride production method, the carboxylic acid anhydrides of heptanoic acid ($C_7$-acid), lauric acid ($C_{12}$-acid) and oleic acid ($C_{18}$-acid) are prepared first, respectively.

For the production of the carboxylic acid anhydride of heptanoic acid ($C_7$-acid), 860 g heptanoic acid are provided in a 2,000-ml-multi-neck flask with dephlegmator (partial condenser) and distillation bridge, and 445 g acetic anhydride are added at 90° C. under stirring. The reaction mixture is then refluxed at 130° C. for 6 h under stirring. The formed acetic acid and the excess acetic anhydride are then distilled off under vacuum. The heptanoic anhydride is obtained. Characterization is carried out by GC and GC-MS.

The carboxylic acid anhydrides of lauric acid ($C_{12}$-acid) and oleic acid ($C_{18}$-acid) are prepared in a corresponding manner.

Subsequently—in accordance with the preparation of 3-acetoxybutyric acid ethyl ester described hereinabove—the carboxylic acid anhydride in question is reacted with 3-BHB ethyl ester, so that in each case the 3-BHB ethyl esters capped with the carboxylic acid anhydride in the 3-position result.

Cleavage experiments (splitting experiments) with these capped 3-BHB ethyl esters each in a gastric or intestinal medium (FaSSGF medium simulating the stomach or FaSSIF medium simulating the intestinal tract), each in the presence or absence of pancreatin, demonstrate cleavage to 3-BHB in free form. These cleavage experiments demonstrate that capped (blocked) 3-hydroxybutyric acid or its salts or esters are efficient precursors or metabolites of free 3-hydroxybutyric acid or its salts, especially with respect to their intended effects, which are moreover in physiologically tolerable or physiologically compatible form.

Further Physiological Application Tests: In-Vitro Digestion Tests

Digestion Experiments (Splitting or Cleavage Experiments) of Inventive Compound

By means of cleavage experiments it is shown that reaction products prepared according to the invention or mixtures thereof can be cleaved in the human gastrointestinal tract. The starting mixture used is, on the one hand, a 3-acetoxybutyric acid ethyl ester obtained and purified by the process according to the invention as described hereinabove and, on the other hand, in each case the 3-BHB ethyl esters capped in the 3-position with the carboxylic acid anhydride (heptanoic acid anhydride, lauric acid anhydride or oleic acid anhydride) obtained and purified by the process according to the invention as described hereinabove.

For the cleavage experiments under near-body conditions two media are investigated:

FaSSGF, which simulates the stomach

FaSSIF, which simulates the intestinal tract

Both media are from the company Biorelevant®, Ltd. in Great Britain. In addition, in some experiments porcine pancreas is added (Panzytrat® 40,000, Fa. Allergan).

The results of the cleavage experiments in a FaSSGF or FaSSIF medium with Panzytrat® and without Panzytrat® (both 35° C., 24 h) show that all samples hydrolyze under FaSSGF conditions with Panzytrat® and without Panzytrat®; this is mainly due to the low pH value (pH=1.6). Under FaSSIF conditions, a lower conversion using Panzytrat® takes place.

All experiments show that the desired free acid 3-BHB is generated. The conversion/time course of the aqueous cleavage of the compounds according to the invention, including the increase in acid number over time, proves the desired decomposition of the educts to the free acid (3-BHB). This is confirmed by appropriate analysis.

The previously described cleavage experiments prove that capped (blocked) 3-hydroxybutyric acid or its salts or esters are efficient precursors or metabolites of free hydroxybutyric acid or its salts, especially with regard to their intended effect, and are also present in a physiologically compatible form.

The invention claimed is:

1. A method for producing capped 3-hydroxybutyric acid or s salts or esters,
wherein at least one compound of the general formula (I)

$$CH_3-CH(OH)-CH_2-C(O)OR^1 \qquad (I)$$

wherein in the general formula (I) the radical $R^1$ represents hydrogen, methyl or ethyl,
is reacted with at least one carboxylic acid anhydride of the general formula (II)

$$R^2-C(O)-O-C(O)-R^3 \qquad (II)$$

wherein in the general formula (II) the radicals $R^2$ and $R^3$, each independently of one another, represent a linear or branched, saturated or mono- or polyunsaturated $C_3$-$C_{21}$-alkyl,
wherein the reaction of the at least one compound of the general formula (I) with the at least one carboxylic acid anhydride of the general formula (II) is carried out in the absence of any solvents,
so that, as reaction product, there is obtained one or more capped 3-hydroxybutyric acids or their salts or esters of the general formula (III)

$$CH_3-CH[O-C(O)R^5]-CH_2-C(O)OR^4 \qquad (III)$$

wherein in the general formula (III) the radical $R^4$ represents methyl, ethyl or a metal ion and the radical $R^5$ represents a radical $R^2$ or $R^3$ each having the meaning defined hereinabove.

2. The method according to claim 1,
wherein the reaction of the at least one compound of the general formula (I) with the at least one carboxylic acid anhydride of the general formula (II) is followed by hydrolysis in the case that $R^1$ represents hydrogen.

3. The method according to claim 2,
wherein the hydrolysis is carried out under acidic or basic conditions.

4. The method according to claim 1,
wherein the compound of general formula (I) is used in racemic form or in the form of the (R)-enantiomer.

5. The method according to claim 1,
wherein, as a compound of the general formula (I), 3-hydroxybutyric acid ethyl ester of the formula $CH_3-CH(OH)-CH_2-C(O)OC_2H_5$ is used.

6. The method according to claim 1,
wherein, as a carboxylic acid anhydride of the general formula (II), a compound in which the radicals $R^2$ and $R^3$ are identical is used.

7. The method according to claim 1,
wherein, as a carboxylic acid anhydride of the general formula (II), a compound in which the radicals $R^2$ and $R^3$ are different from one another is used.

8. The method according to claim 1,
wherein the reaction of the at least one compound of the general formula (I) with the at least one carboxylic acid anhydride of the general formula (II) is carried out at temperatures in the range of from 60 to 150° C.; and
wherein the reaction of the at least one compound of the general formula (I) with the at least one carboxylic acid anhydride of the general formula (II) is carried out at a pressure in the range of from 0.0001 bar to 10 bar.

9. The method according to claim 1,
wherein during the reaction of the at least one compound of the general formula (I) with the at least one carboxylic acid anhydride of the general formula (II), a compound of the general formula (IV)

$$R^5-C(O)-OH \qquad (IV)$$

is formed simultaneously, wherein the radical $R^5$ has the meaning defined hereinabove;
wherein the compound of the general formula (IV) is removed during or after the reaction has taken place.

10. The method according to claim 1,
wherein the reaction of the at least one compound of the general formula (I) with the at least one carboxylic acid anhydride of the general formula (II) is followed by purification;
wherein any starting compounds and reaction by-products still present are distilled off.

11. The method according to claim 1,
wherein, as a reaction product, one or more capped (blocked) 3-hydroxybutyric acid salts and/or esters of the general formula (III)

$$CH_3-CH[O-C(O)R^5]CH_2-C(O)OR^4 \qquad (III)$$

is formed,
wherein in the general formula (III)
the radical $R^4$ represents methyl or ethyl,
the radical $R^5$ represents a linear or branched, saturated or mono- or polyunsaturated $C_3$-$C_{21}$-alkyl.

12. The method according to claim 1,
wherein, as a reaction product, one or more capped (blocked) 3-hydroxybutyric acid salts and/or esters of the general formula (III)

$$CH_3-CH[O-C(O)R^5]-CH_2-C(O)OR^4 \qquad (III)$$

is formed,
wherein in the general formula (III)
the radical $R^4$ represents ethyl,
the radical $R^5$ represents a linear or branched, saturated or mono- or polyunsaturated $C_3$-$C_{21}$-alkyl.

* * * * *